(12) United States Patent
Branscome et al.

(10) Patent No.: US 10,285,714 B2
(45) Date of Patent: May 14, 2019

(54) ASSEMBLY AND SYSTEM INCLUDING A TIBIAL CUT GUIDE

(71) Applicant: Biomet Manufacturing, LLC, Warsaw, IN (US)

(72) Inventors: Douglas G Branscome, Fort Wayne, IN (US); Duke A. Fox, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 251 days.

(21) Appl. No.: 15/266,311

(22) Filed: Sep. 15, 2016

(65) Prior Publication Data

US 2018/0070960 A1    Mar. 15, 2018

(51) Int. Cl.
*A61B 17/15* (2006.01)
*A61B 90/00* (2016.01)

(52) U.S. Cl.
CPC ............ *A61B 17/157* (2013.01); *A61B 90/06* (2016.02); *A61B 2090/061* (2016.02)

(58) Field of Classification Search
CPC .................................................. A61B 17/157
See application file for complete search history.

(56) References Cited

U.S. PATENT DOCUMENTS

| 5,628,750 | A  | 5/1997  | Whitlock et al. |
| 7,641,663 | B2 | 1/2010  | Hodorek |
| 8,317,797 | B2 | 11/2012 | Rasmussen |
| 8,758,354 | B2 | 6/2014  | Habegger et al. |

(Continued)

FOREIGN PATENT DOCUMENTS

| CN | 107920825 | 4/2018 |
| GB | 2480846   | 12/2011 |

(Continued)

OTHER PUBLICATIONS

"International Application Serial No. PCT/US2017/050957, International Search Report dated Jan. 24, 2018", 6 pgs.

(Continued)

*Primary Examiner* — Andrew Yang
(74) *Attorney, Agent, or Firm* — Schwegman Lundberg & Woessner, P.A.

(57) ABSTRACT

Systems and apparatuses including a system that can be used in a knee replacement procedure are disclosed. According to one example, the system can include a tibial cut guide and an alignment guide. The tibial cut guide can have a first guide portion coupled to and adjustable relative to a second guide portion. The first guide portion can be configured to define a sagittal cut slot and the second guide portion can be configured to define a proximal cut slot. The alignment guide can be configured for extramedullary mounting to the patient and can be configured to couple with the second guide portion of the tibial cut guide. The alignment guide can have a first mechanism and a second mechanism of differing construction. The first mechanism and the second mechanism can both be configured to be actuated to facilitate extension and retraction of the alignment guide to position the tibial cut guide in a desired proximal-distal location relative a tibia of a patient when the tibial cut guide and the alignment guide are assembled together.

19 Claims, 17 Drawing Sheets

(56) References Cited

U.S. PATENT DOCUMENTS

| | | | |
|---|---|---|---|
| 2006/0184173 | A1 | 8/2006 | Collazo |
| 2007/0233138 | A1 | 10/2007 | Figueroa et al. |
| 2012/0179266 | A1 | 7/2012 | Collazo |
| 2013/0204260 | A1 | 8/2013 | Dietzel et al. |
| 2014/0066934 | A1* | 3/2014 | Deirmengian ..... A61B 17/1764 606/83 |
| 2015/0196308 | A1 | 7/2015 | Wilkinson et al. |
| 2015/0342742 | A1 | 12/2015 | Ferro et al. |
| 2016/0367271 | A1 | 12/2016 | Jones et al. |
| 2017/0135708 | A1 | 5/2017 | Jaumard et al. |
| 2018/0070961 | A1 | 3/2018 | Branscome et al. |

FOREIGN PATENT DOCUMENTS

| | | |
|---|---|---|
| WO | 2008091358 | 7/2008 |
| WO | 2012158604 | 11/2012 |
| WO | 2013063375 | 5/2013 |
| WO | 2016205454 | 12/2016 |
| WO | 2018052843 | 3/2018 |

OTHER PUBLICATIONS

"International Application Serial No. PCT/US2017/050957, Written Opinion dated Jan. 24, 2018", 10 pgs.

"International Application Serial No. PCT/US2017/050957, Invitation to Pay Additional Fees and Partial Search Report dated Nov. 21, 2017", 13 pgs.

U.S. Appl. No. 15/184,016, filed Jun. 16, 2016, Tibial Cut Guide.

"International Application Serial No. PCT/US2016/037765, Invitation to Pay Additional Fees and Partial Search Report dated Sep. 9, 2016", 7 pgs.

"International Application Serial No. PCT/US2016/037765, International Search Report dated Nov. 21, 2016", 5 pgs.

"International Application Serial No. PCT/US2016/037765, Written Opinion dated Nov. 21, 2016", 8 pgs.

"U.S. Appl. No. 15/184,016, Non Final Office Action dated May 2, 2018", 16 pgs.

U.S. Appl. No. 15/341,306, field Nov. 2, 2016, Assembly for a Tibial Cut Guide.

U.S. Appl. No. 15/693,723, filed Sep. 1, 2017, Assembly and System Including a Tibial Cut Guide.

"U.S. Appl. No. 15/184,016, Advisory Action dated Nov. 5, 2018", 3 pgs.

"U.S. Appl. No. 15/184,016, Final Office Action dated Aug. 29, 2018", 15 pgs.

"U.S. Appl. No. 15/184,016, Response Filed Oct. 29, 2018 to Final Office Action dated Aug. 29, 2018", 15 pgs.

"U.S. Appl. No. 15/341,306, Response filed Nov. 9, 2018 to Non Final Office Action dated Aug. 28, 2018", 15 pgs.

"European Application Serial No. 16732186.8, Response filed Sep. 3, 2018 to Office Action dated Feb. 20, 2018", 16 pgs.

"U.S. Appl. No. 15/341,306, Notice of Allowance dated Nov. 29, 2018", 6 pgs.

"U.S. Appl. No. 15/693,723, Non Final Office Action dated Nov. 30, 2018", 8 pgs.

"U.S. Appl. No. 15/184,016, Response filed Aug. 8, 2018 to Non Final Office Action dated May 2, 2018", 15 pgs.

U.S. Appl. No. 15/341,306, Non Final Office Action dated Aug. 28, 2018, 8 pgs.

\* cited by examiner

ASSEMBLY AND SYSTEM INCLUDING A TIBIAL CUT GUIDE

FIELD

The present subject matter relates to orthopedic procedures and, more particularly, to an assemblies and systems that can aid in bone resection for knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

The present inventors recognize the need for an extramedullary alignment guide that can be used to quickly and accurately position (with regard to proximal-distal location, varus-valgus location, sagittal cut angle and medial-lateral location, and/or posterior slope angle) a tibial cut guide for removal of the articular surfaces of the tibia. The present inventors also recognize that the alignment guide can be provided a feature to make small adjustments to the proximal-distal location of the tibial cut guide once the alignment guide has already been fixated to the tibia can further reduce procedure time and improve accuracy. The inventors further recognize that the tibial cut guide can have a separate second portion defining a sagittal cut slot. This second portion can be adjustable relative to a remainder of the tibial cut guide (and indeed the alignment guide) to adjust a location and rotation angle of the sagittal cut. The tibial cut guide with the adjustable portion can allow for adjustment of the location and rotation angle of the sagittal cut after determining a desired proximal-distal location, varus-valgus location, and/or posterior slope angle for the tibial cut guide. This can allow for quicker and simpler adjust of the tibia cut guide to a desired position to perform resection. Further, the inventors recognize the need to adjust a proximal-distal position of the tibial cut guide in a rapid manner. Thus, one or more connections between portions of the alignment guide can be "quick-connect" or "quick-release" in nature to facilitate quick and accurate assembly, disassembly, positioning, and repositioning of the alignment guide and tibial cut guide.

To further illustrate the apparatuses and systems disclosed herein, the following non-limiting examples are provided:

Example 1 is a system for a knee replacement surgery that can include a tibial cut guide that can have a first guide portion coupled to and adjustable relative to a second guide portion and an alignment guide. The first guide portion can be configured to define a sagittal cut slot and the second guide portion can be configured to define a proximal cut slot. The alignment guide can be configured for extramedullary mounting to the patient and can be configured to couple with the second guide portion of the tibial cut guide. The alignment guide can have a first mechanism and a second mechanism of differing construction. The first mechanism and the second mechanism can both configured be actuated to facilitate extension and retraction of the alignment guide to position the tibial cut guide in a desired proximal-distal location relative a tibia of a patient when the tibial cut guide and the alignment guide are assembled together.

In Example 2, the subject matter of Example 1 can optionally include the alignment guide has a proximal assembly and a distal assembly. The distal assembly can include a rod having one or more engagement features along at least a portion thereof. The proximal assembly can be configured to be moveable relative to the distal assembly and can include a slot configured to receive at least a part of the rod therein. The proximal assembly can have an arm extending proximally, the arm can be configured to receive a fastener therein to couple the alignment guide to the tibia of the patient.

In Example 3, the subject matter of Example 2 can optionally include the distal assembly can be configured to couple with the first mechanism which can comprise a button that is configured to be depressible to facilitate adjustment of the proximal assembly relative to the distal assembly. The button can be configured to engage the one or more engagement features of the distal assembly.

In Example 4, the subject matter of any one or more of Examples 2-3 can optionally include wherein the proximal assembly can have a first body and a second body, and the first body can be moveable relative to the second body by the second mechanism.

In Example 5, the subject matter of Example 4 can optionally include the second mechanism can comprise a thumb screw configured to threadably engage the first body and be received within a recess of the second body.

In Example 6, the subject matter of Example 5 can optionally include wherein the thumb screw can be configured to retain one or more ball plunger assemblies and the second body can be configured with one or more grooves that can be configured to interact with the one or more ball plunger assemblies to act as indicia of a degree of movement of the second mechanism and an amount of proximal-distal travel of the first body relative to the second body.

In Example 7, the subject matter of any one or more of Examples 2-6 can optionally include both the first body and the second body can have indicia that when used together can be indicative of an amount of proximal-distal travel of the first body relative to the second body.

In Example 8, the subject matter of any one or more of Examples 1-7 can optionally include the first guide portion of the tibial cut guide can be configured to be adjustable both with respect to a medial-lateral position and a rotational position relative to the second guide portion.

In Example 9, the subject matter of any one or more of Examples 1-8 can optionally include the second guide portion can define a recess relative to the proximal cut slot. The recess can be configured to receive the first guide portion therein. The recess can at least partially be defined by anterior-posterior spaced projections configured to receive a pin therein. A leg of the first guide portion can be configured to insert between the anterior-posterior spaced projections and beneath the pin.

In Example 10, the subject matter of any one or more of Examples 1-9 can optionally include the sagittal cut slot communicates with an aperture. The aperture can be configured to receive a fastener therein to fix the first guide portion relative to the tibia and the second guide portion.

In Example 11, the subject matter of any one or more of Examples 1-10 can optionally include the proximal cut slot can be offset from a mount of the second guide portion in at least one of a medial or lateral direction and the proximal cut slot can be configured to define a medial-lateral cut length such that the proximal cut is to a single compartment of a knee.

Example 12 is an apparatus for guiding a tibial bone cut during knee replacement surgery, the apparatus can include a mount configured to couple with an alignment guide. A proximal guide portion can be connected to the mount and can be configured to define a proximal cut slot. The proximal cut slot can be offset from the mount in at least one of a medial or lateral direction and the proximal cut slot can be configured to define a medial-lateral cut length such that the proximal cut is to a single compartment of a knee. A sagittal guide portion can be coupled to and adjustable relative to the proximal guide portion. The sagittal guide portion can be configured to define a sagittal cut slot.

In Example 13, the subject matter of Example 12 can optionally include the sagittal guide portion can be configured to be adjustable both with respect to a medial-lateral position and a rotational position relative to the proximal guide portion.

In Example 14, the subject matter of any one or more of Examples 12-13 can optionally include the proximal guide portion can define a recess relative to the proximal cut slot. The recess can be configured to receive the sagittal guide portion therein. The recess can at least partially be defined by anterior-posterior spaced projections configured to receive a pin therein. A leg of the sagittal guide portion can be configured to insert between the anterior-posterior spaced projections and beneath the pin.

In Example 15, the subject matter of any one or more of Examples 1-14 can optionally include the sagittal cut slot can communicate with an aperture. The aperture can be configured to receive a fastener therein to fix the first guide portion relative to the tibia.

Example 16 is an alignment guide configured for extramedullary mounting to a patient for a knee replacement surgery, the alignment guide can include a first portion, a second portion, a first mechanism, a second mechanism, and a third portion. The first portion can have a rod with one or more engagement features along at least a portion thereof. The second portion can be moveable relative to the first portion and can have a slot configured to receive at least a part of the rod therein. The second portion can configured to receive at least a part of the first mechanism and the second mechanism. The first mechanism can be configured to be actuated facilitate proximal-distal adjustment of the second portion relative to the first portion. The third portion can at least partially received by the second portion and can be moveable relative thereto. The third portion can be configured to couple with a tibial cut guide. The second mechanism can be configured to be actuated to facilitate proximal-distal adjustment of the third portion relative to the second portion.

In Example 17, the subject matter of Example 16 can optionally include the first adjustment member and the second mechanism can have a differing construction but are both configured to allow the alignment guide to be extended and retracted to position the tibial cut guide in a desired proximal-distal location relative a tibia of a patient.

In Example 18, the subject matter of any one or more of Examples 16-17 can optionally include the second portion can have an arm configured to receive a fastener therein to couple the alignment guide to the tibia of the patient.

In Example 19, the subject matter of any one or more of Examples 16-18 can optionally include the second mechanism comprises a thumb screw that can be configured to threadably engage the third portion and be received within a recess of the second portion.

In Example 20, the subject matter of any one or more of Examples 17-19 can optionally include the thumb screw can be configured to retain one or more ball plunger assemblies and the second portion can be configured with one or more grooves that interact with the one or more ball plunger assemblies to act as indicia of a degree of movement of the second mechanism and an amount of proximal-distal travel of the third portion relative to the second portion.

In Example 21, the subject matter of any one or more of Examples 16-20 can optionally include both the third portion and the second portion can have indicia that when used together can be indicative of an amount of proximal-distal travel of the third portion relative to the second portion.

Example 22 is a method of performing a tibial knee resection that can include any one or combination of the following steps: mounting a tibial cut guide to an alignment mechanism, the tibial cut guide configured to facilitate both a proximal cut and a sagittal cut to a tibia; adjusting a proximal-distal location and varus-valgus location for a first slot that is used to define the proximal cut; fixating a first portion the alignment guide to the tibia of the patient; after fixating the first portion of the alignment guide to the tibia, adjusting a proximal-distal height of the cut guide by extending or retracting a second portion of the alignment guide relative to the first portion of the alignment guide; after adjusting the proximal-distal height of the cut guide, adjusting at least one of a medial-lateral location and a rotational angle of a second slot that is used to define the sagittal cut by moving a first guide portion of the tibial cut guide relative to a second guide portion with reference to one or more anatomical landmarks of the knee; and resecting the tibia by performing both the proximal cut and the sagittal cut utilizing the tibial cut guide.

In Example 23, the subject matter of Example 22 can optionally include fixating the first guide portion to the tibia prior to resecting the tibia.

In Example 24, the subject matter of any one or more of Examples 22-23 can optionally include the anatomical landmarks can include one or more of the intercondylar eminence of the tibia, a connection position of an ACL with the tibia, a medial third of a tubercle at insertion of a PCL, and an intercondylar geometry of a femur.

In Example 25, the apparatuses, systems and methods of any one or any combination of Examples 1 to 24 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for knee replacement procedures. For example, the present application discloses a tibial alignment guide that can position a tibial cut guide for removal of the articular surfaces of the tibia.

Figure 1:
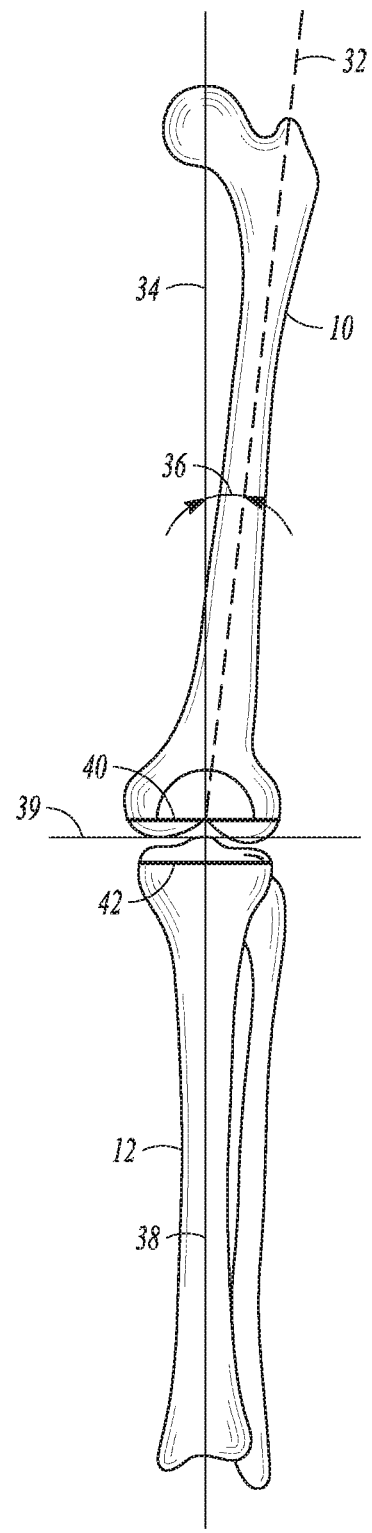
FIG. 1 is a front elevation view of a tibia and a femur showing axes of the knee joint according to an example of the present application.

FIG. 1 illustrates various axes of the lower limb in the frontal plane. Axes can be defined for each segment of the lower limb. For example, a femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane. Likewise, a tibia 12 has a mechanical axis 38 coinciding generally with its intramedullary canal. The mechanical axis 38 of the tibia 12 runs from the center of the knee to the center of the ankle. The transverse axis, or joint line 39, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

A distal femoral cut can be made perpendicular to the femoral axes 32, 34 in the sagittal plane. A proximal tibial resection is typically cut to match the natural posterior slope of the proximal tibia in the sagittal plane, relative to the mechanical axes 34, 38. The amount of posterior to anterior slope (also referred to herein as posterior slope angle) relative perpendicular to the mechanical axes 34, 38 varies in the patient population but is on the order of 2° to 7°. The distance between the distal femoral cut and proximal tibial cut along the mechanical axes 34, 38 is the extension gap. Other cuts may be made depending on the components that are to be implanted and the type of procedure performed.

As used herein, "proximal" refers to a direction generally toward the torso of a patient, and "distal" refers to the opposite direction of proximal, i.e., away from the torso of a patient. "Anterior" refers to a direction generally facing away from the patient, i.e. toward the surgeon performing the surgery, and "posterior" refers to the opposite direction of anterior, i.e., toward the front (anterior) of a patient or knee. In the context of the tibial alignment guide and tibial cut guide such as those disclosed herein, such directions correspond to the orientation of these when in use (i.e. when mounted to or adjacent the patient in an operable position to assist in making desired resections), such that a proximal assembly of the assembly is that portion which will ordinarily be closest to the torso of the patient, the anterior portion closest to the surgeon, the posterior portion generally closest to the anterior portion of the patient's knee, etc.

Figure 2:
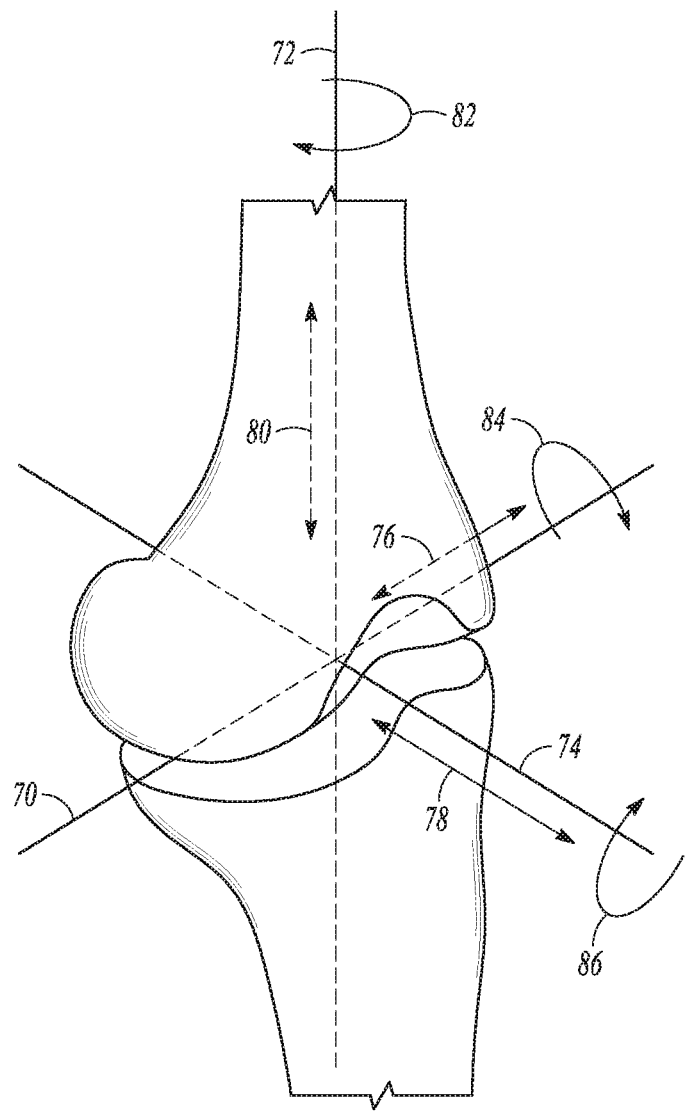
FIG. 2 is an elevated perspective view of the tibia and femur showing various axes of the knee joint according to the example of the present invention.

FIG. 2 depicts six aspects of component positioning relative to a coordinate system in which the x-axis 70 (media-lateral axis) corresponds approximately to the joint line 39, the z-axis 72 (proximal-distal axis) corresponds approximately to the mechanical axes 34 and 38, and the y-axis 74 (anterior-posterior axis) is normal to the other two. Position along each of these axes is depicted by arrows. Position along the x, y, and z axes determines the medial-lateral (dx) 76, anterior-posterior (dy) 78, and proximal-distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 3:
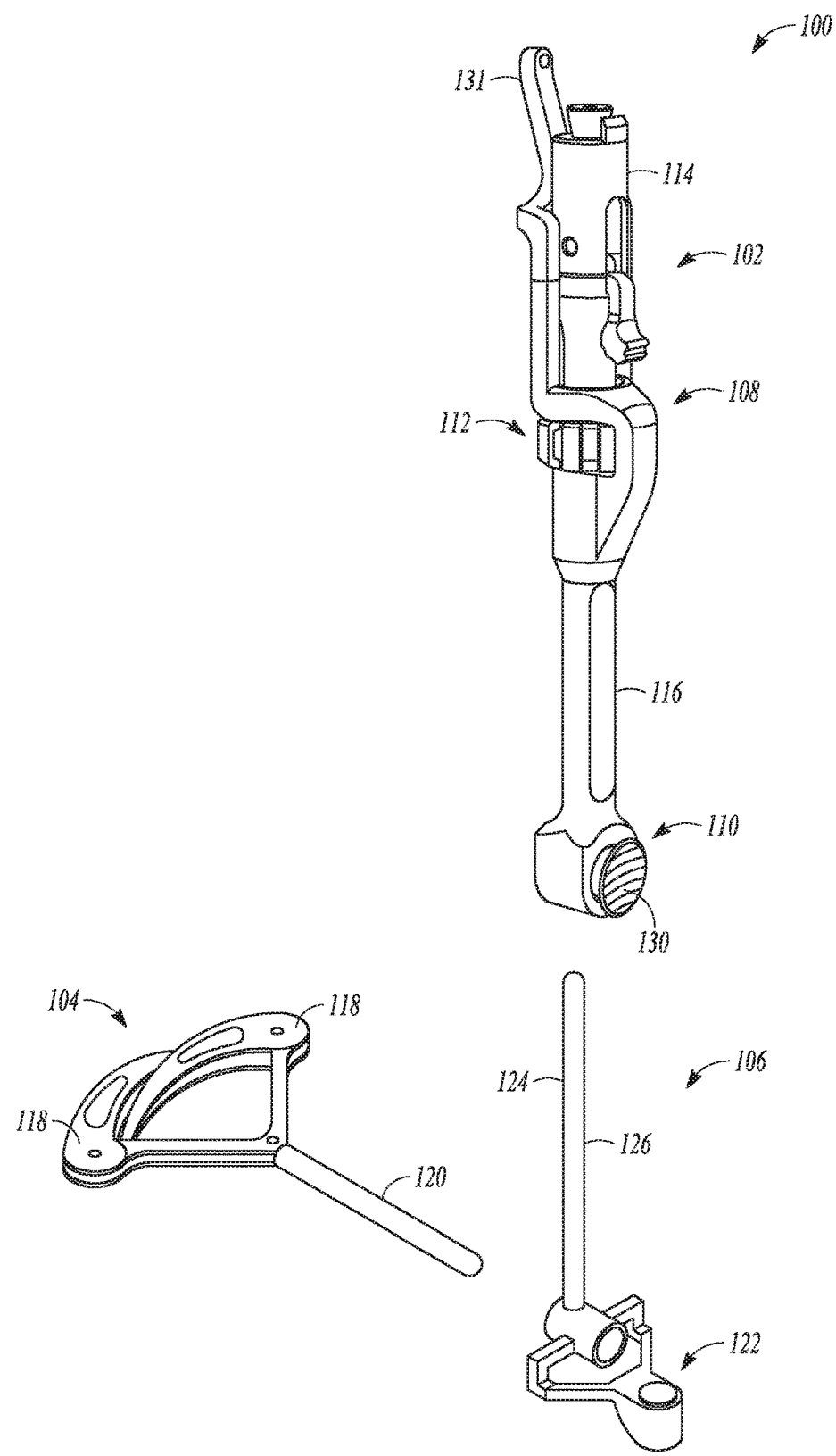
FIG. 3 is a perspective view of a disassembled extramedullary tibial alignment guide according to an example of the present invention.

FIG. 3 shows a system 100 according to one example of the present disclosure. When assembled the system 100 can comprise a tibial alignment guide 102 configured for extramedullary mounting to a patient. The system 100 can include an ankle clamp 104, a distal assembly 106, a proximal assembly 108, a first mechanism 110 and a second mechanism 112. The proximal assembly 108 includes a first body 114 and a second body 116.

As shown the ankle clamp 104 can be configured to connect to the distal assembly 106. The distal assembly 106 can be adjustable anterior-posterior relative to the ankle clamp 104. The distal assembly 106 can have a portion extending generally proximal-distal when assembled. The proximal assembly 108 can be configured to be mounted on and moveable relative distal assembly 106. For example, the proximal assembly 108 can receive the portion of the distal assembly 106 and can be adjustable generally proximal-distal relative to the distal assembly 106 via actuation of the first and/or second mechanisms 110, 112 as will be discussed subsequently. Such adjustment of the proximal assembly 108 can allow the tibial alignment guide 102 to be extended and retracted to position a tibial cut guide in a desired proximal-distal location relative a tibia of a patient when the tibial cut guide and the alignment guide 102 are assembled together as will be further discussed subsequently.

The ankle clamp 104 can be configured with spring arms 118 adapted to clamp around an ankle of the patient such as proximal to the malleoli. The ankle clamp 104 can include a rod 120 that can have one or more engagement features (e.g., threads, slots, detents, teeth, etc.) along at least a portion thereof. The distal assembly 106 can be configured to receive the rod 120 therein. The distal assembly 106 can have a third mechanism 122 that can receive the rod 120 therein. The third mechanism 122 can be configured as a quick connect to couple with the one or more engagement features to fixedly connect the distal assembly 106 to the ankle clamp 104. The third mechanism 122 can be configured to be actuated by the user to disengage the third mechanism 122 from the engagement feature(s) to allow for adjustment of the position of the distal assembly 106 relative to the ankle clamp 104. Such adjustment can be facilitated by depressing and holding a button or similar feature of the third mechanism 122, for example.

As shown in the example of FIG. 3, the distal assembly 106 can include a rod 124 configured to extend generally proximal-distal when assembled with the ankle clamp 104. The rod 124 can have one or more engagement features 126 (e.g., threads, slots, detents, teeth, etc.) along at least a portion thereof. The proximal assembly 108 can include a slot 128 (FIG. 5B) configured to receive at least a part of the rod 124 therein.

Figure 5A:
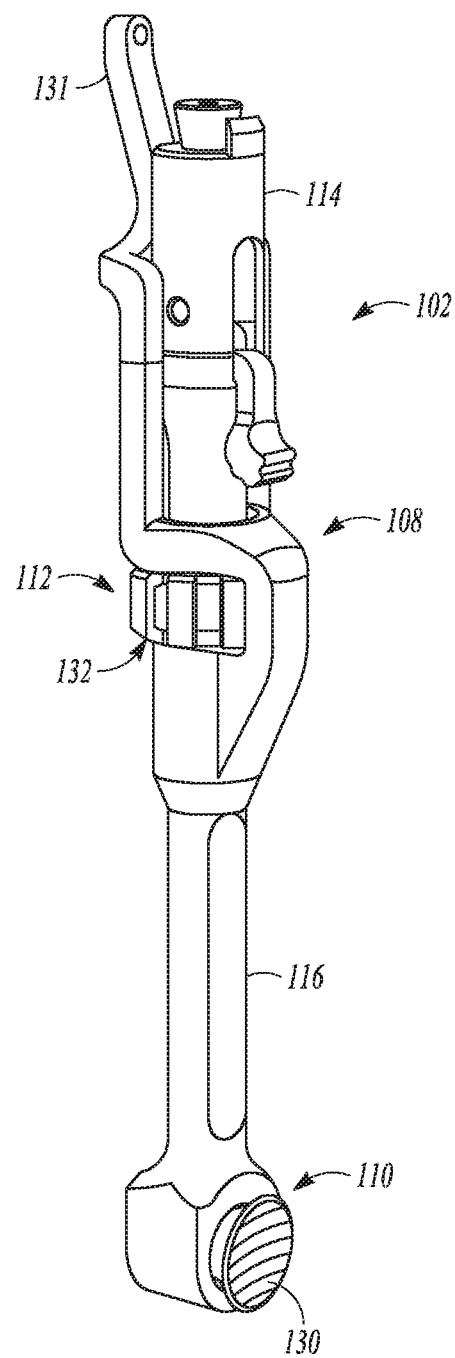
FIG. 5A is a perspective view of an anterior side of a proximal assembly of the tibial alignment guide of FIG. 3 according to an example of the present application.

As shown in FIGS. 3 and 5A, the first mechanism 110 can be carried by the proximal assembly 108 at a distal portion thereof, for example. The first mechanism 110 that can receive the rod 124 (FIG. 3) therein. The first mechanism 110 can be configured to couple with the one or more engagement features 126 (FIG. 3) to fixedly connect the proximal assembly 108 to the distal assembly 106. The first mechanism 110 can be configured to be actuated by the user to disengage the first mechanism 110 from the one or more engagement features 126 (FIG. 3) to allow for adjustment of the position of the proximal assembly 108 generally proximal-distal relative to the distal assembly 106. Such adjustment can be facilitated by depressing and holding a button 130 or similar feature of the first mechanism 110, for example.

In the example of FIGS. 3 and 5A, the proximal assembly 108 can be comprised of the first body 114 and the second body 116. The proximal assembly 108 (in particular the second body 116) can also include an arm 131 extending proximally. The arm 131 can be configured to receive a fastener (not shown) or other component therein to couple the tibial alignment guide 102 to the tibia of the patient. The second body 116 can carry the first mechanism 110. The second mechanism 112 can be received within a recess 132 (FIG. 5A) of the second body 116 proximal of the first mechanism 110. The second mechanism 112 can be carried on the first body 114, and indeed can be threadably engaged thereto with inter-engaging threads as will be discussed subsequently.

The first body 114 can be moveable relative to the second body 116 by the second mechanism 112. Such movement of the first body 114 relative to the second body 116 can facilitate extension and retraction of the tibial alignment guide 102 to position the tibial cut guide in a desired proximal-distal location relative a tibia of a patient when the tibial cut guide and the alignment guide 102 are assembled together. FIGS. 3 and 5A show an example where the first mechanism 110 and the second mechanism 112 can be of differing construction (i.e. have different structure and operate according to different principles when actuated).

Figure 4:
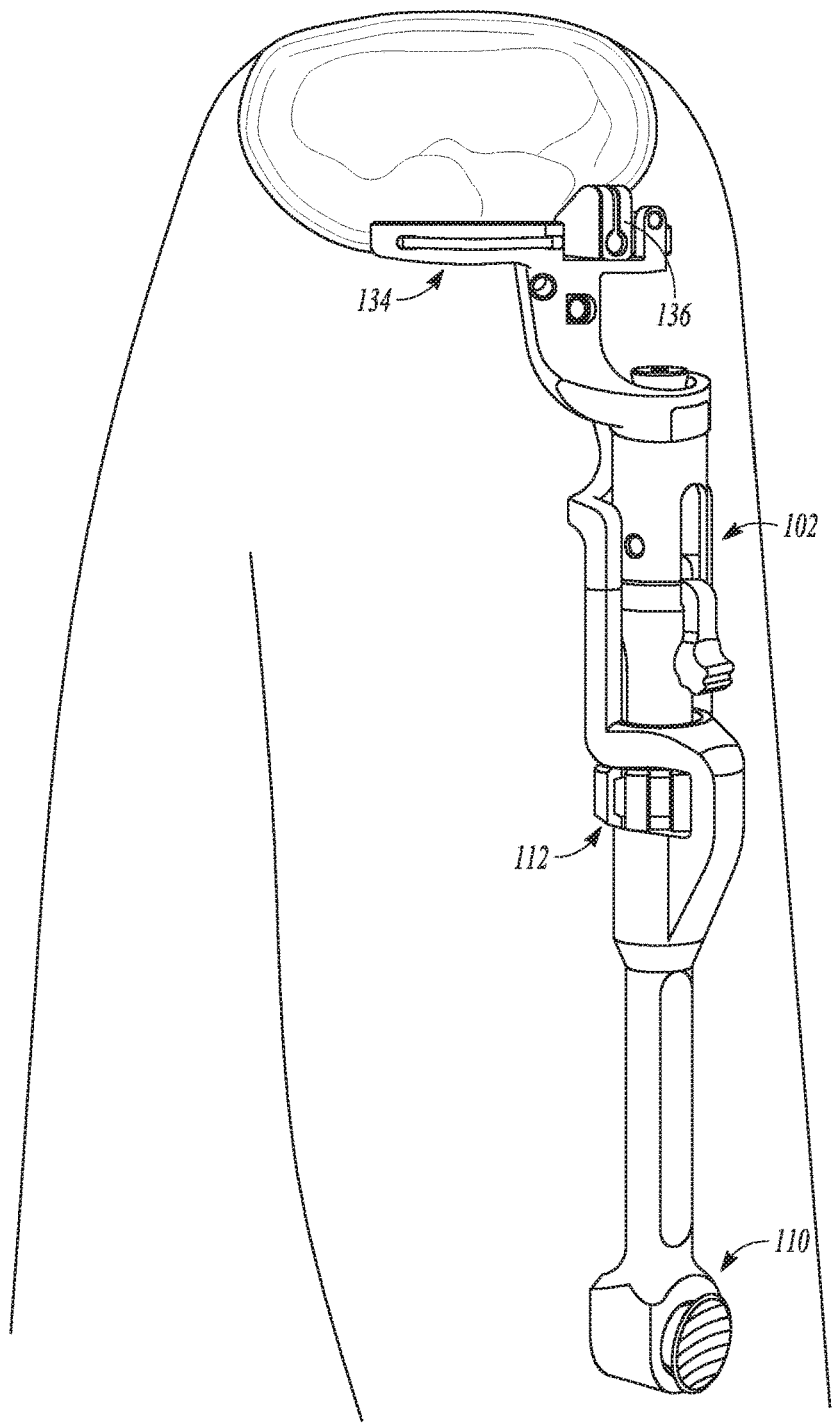
FIG. 4 is a perspective view of the tibial alignment guide being used to position a tibial cut guide relative to a tibia of a patient of according to an example of the present application.

As shown in FIG. 4, the first mechanism 110 and the second mechanism 112 can both be configured to be actuated to facilitate generally proximal-distal movement of tibial alignment guide 102. In particular, the first mechanism 110 and the second mechanism 112 can both be configured to be actuated to facilitate extension and retraction of the tibial alignment guide 102 to position the tibial cut guide 134 in a desired proximal-distal location relative a tibia 136 of a patient when the tibial cut guide 134 and the tibial alignment guide 102 are assembled together.

Figure 5B:
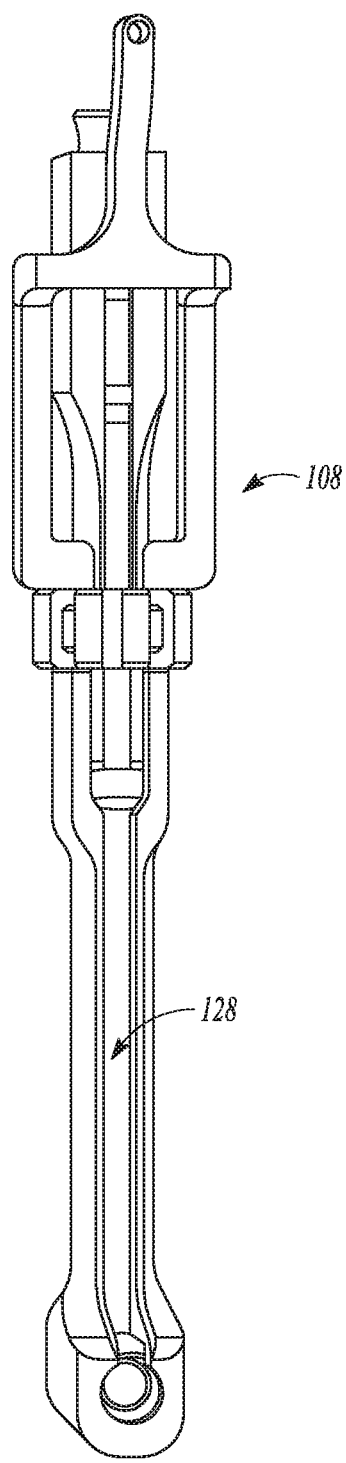
FIG. 5B is a perspective view of a posterior side of a proximal assembly of the tibial alignment guide of FIG. 5A according to an example of the present application.
Figure 6A:
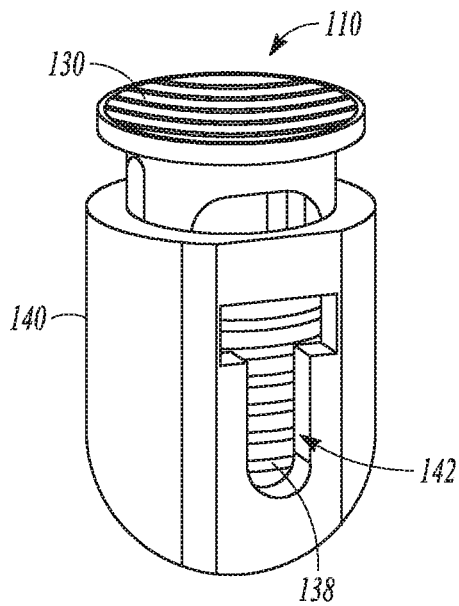
FIG. 6A is a perspective view of a first mechanism of at a distal end of the proximal assembly of the tibial alignment guide of FIGS. 5A and 5B according to an example of the present application.

As shown in FIGS. 5B and 6A, the proximal assembly 108 can include the slot 128 configured to receive at least a part of the rod 124 (FIG. 3) of the distal assembly 106 (FIG. 3) therein. The first mechanism 110 can be configured to engage with the one or more engagement features 126 (e.g., threads, slots, detents, teeth, etc.) along at least a portion of the rod 124 (FIG. 3). This engagement can create a fixed connection between the proximal assembly 108 and the distal assembly 106 until the first mechanism 110 is disengaged by actuation by the user.

Figure 6B:
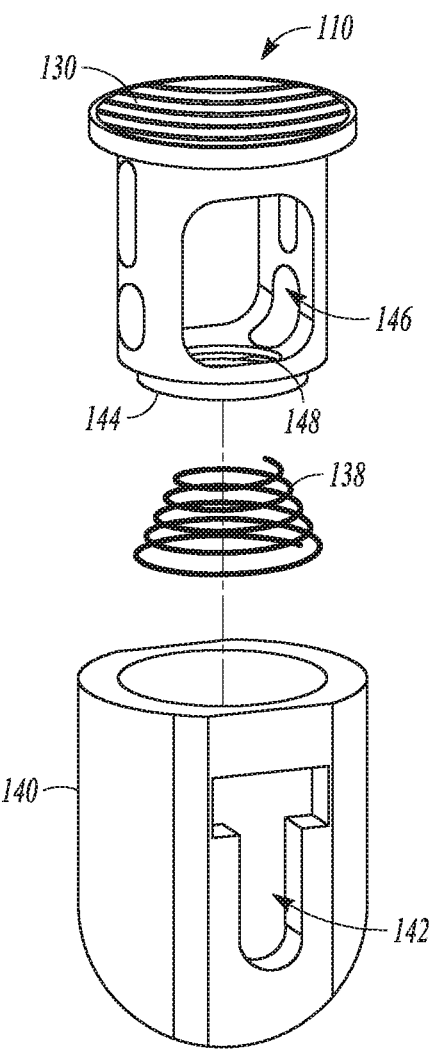
FIG. 6B is an exploded view of the first mechanism of FIG. 6A according to an example of the present application.

As shown in FIGS. 6A and 6B, the first mechanism 110 can comprise the button 130, a spring 138 and a housing 140. The housing 140 can define an opening 142 to the slot 128.

The housing 140 can be configured to receive the rod 124 (FIG. 3) therethrough via the opening 142 defined by the housing 140. The rod 124 (FIG. 3) can be T-shaped to match the slot 128 (FIG. 5B) and opening 142 according to one example. The housing 140 can further include an open end that is configured to receive a portion of the button 130 therein. The spring 138 (e.g., a conical compression spring) can be positioned between an end portion 144 (FIG. 6B) of the button 130 and an interior surface of the housing 140. As shown in FIG. 6B, the button 130 can define an interior passage 146 proximal of and communicating with the opening 142. The interior passage 146 can be provided with threading 148 configured to engage with the one or more engagement features 126 of the rod 124 (FIG. 3).

The button 130 can be configured to be depressible to facilitate adjustment of the proximal assembly 108 relative to the distal assembly 106. As previously discussed, the button 130 can be configured to engage the one or more engagement features 126 (FIG. 3) of the distal assembly 106 (FIG. 3). The configuration of the first mechanism 110 can facilitate fast assembly and adjustment of the tibial cut guide to a desired position. Upon release of the button 130, the spring 138 can push the inner threading 148 of the interior surface of the interior passage 146 into engaging contact with the one or more engagement features 126 of the rod 124 (FIG. 3) to lock the position of the posterior assembly 108 (and in particular the second body 116) relative to the distal assembly 106 (FIG. 3).

Figure 7:
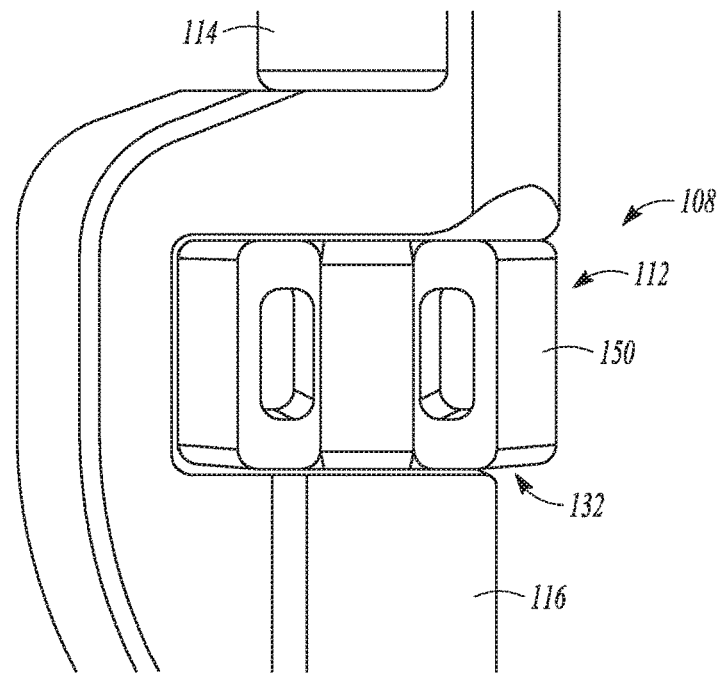
FIG. 7 is an enlarged view of the proximal assembly of the tibial alignment guide showing a second mechanism according to an example of the present application.

FIG. 7 shows an enlargement of a portion of the proximal assembly 108 and the second mechanism 112. As shown in FIG. 7, the second mechanism 112 can comprise a thumb screw 150 configured to threadably engage (with threading 151 shown in FIGS. 7A and 7B) the first body 114 and be received within the recess 132 of the second body 116.

Figure 7A:
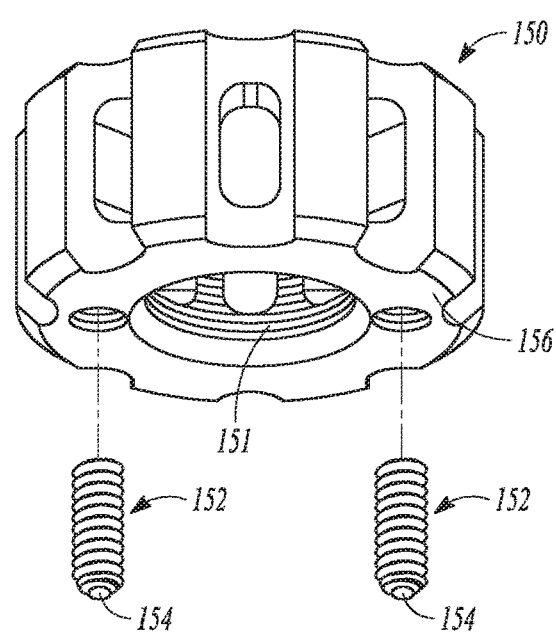
FIG. 7A is exploded view of the second mechanism in isolation from the remainder of the tibial alignment guide according to an example of the present application.
Figure 7B:
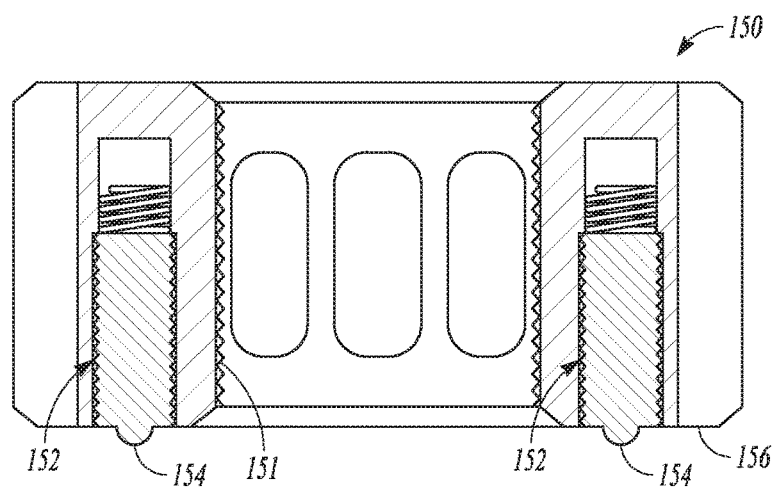
FIG. 7B is a cross-sectional view of the second mechanism according to an example of the present application.
Figure 7C:
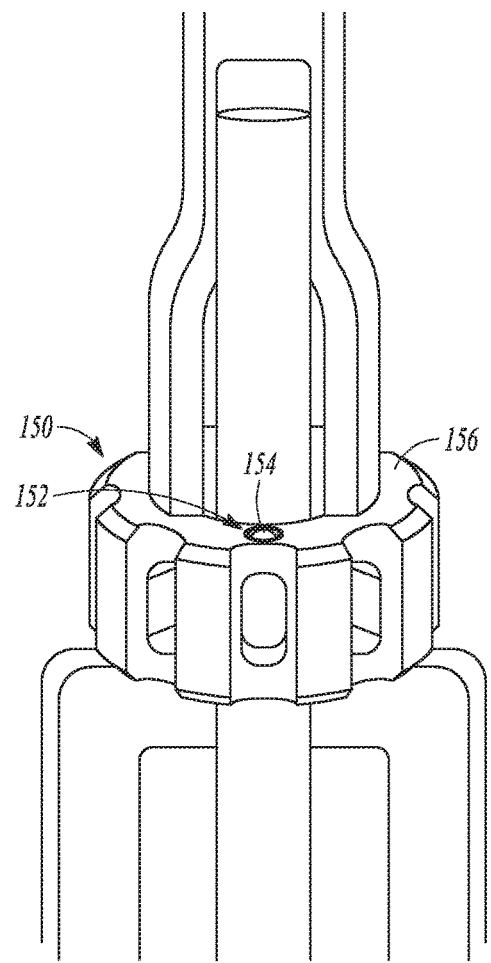
FIG. 7C is a perspective view of a distal assembly of the second mechanism showing a ball plunger extending at least partially thereform according to an example of the present application.

As shown in FIGS. 7A to 7C, the thumb screw 150 can be configured to retain one or more ball plunger assemblies 152 therein such that only a ball portion 154 of the one or more ball plunger assemblies 152 can protrude from a distal surface 156 of the thumb screw 150.

Figure 7D:
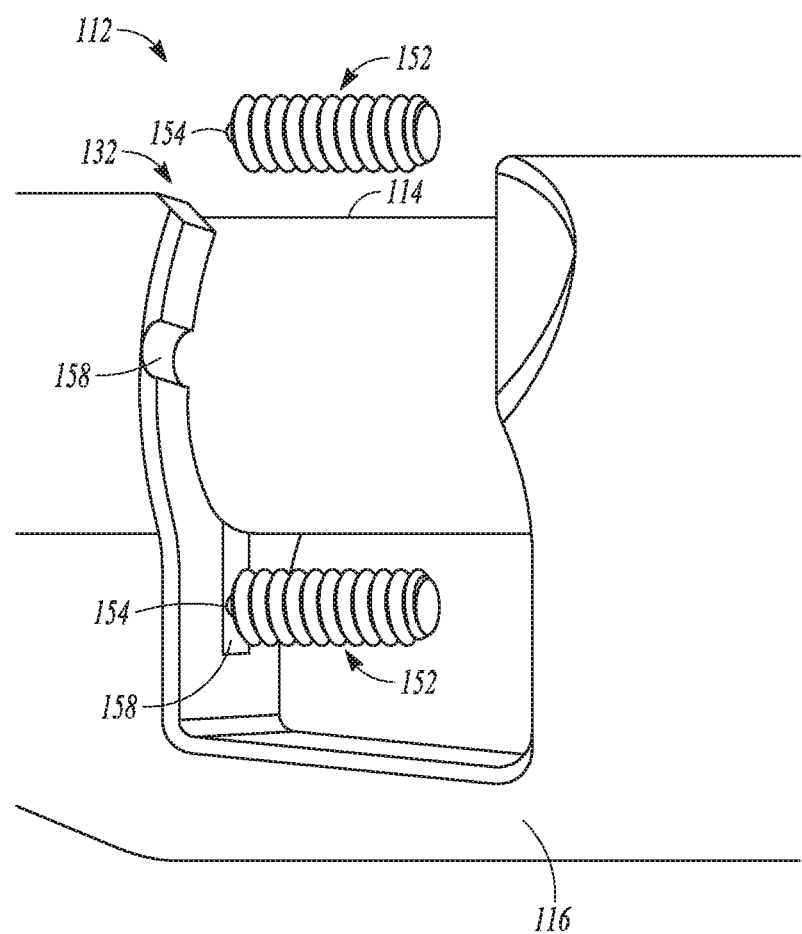
FIG. 7D is a perspective view with portions of the second mechanism removed to show the orientation of the ball plunger relative to the tibial alignment guide according to an example of the present application.

In FIG. 7D, the thumb screw is removed to illustrate the positioning of the one or more ball plunger assemblies 152 within the recess 132 of the second body 116 about the first body 114. As shown in the example of FIG. 7D, the second body 116 can configured with one or more grooves 158 that are configured to interact with the one or more ball plunger assemblies 152 (in particular the ball portion 154) to act as indicia of a degree of movement of the second mechanism 112 and an amount of proximal-distal travel of the first body 114 relative to the second body 116. For example, the one or more grooves 158 and the one or more ball plunger assemblies 152 can interact to make a clicking noise to indicate 90 degrees of rotational movement of the second mechanism 112, and further, the clicking noise can indicate 1 mm of proximal-distal travel of the first body 114 relative to the second body 116.

Figure 8A:
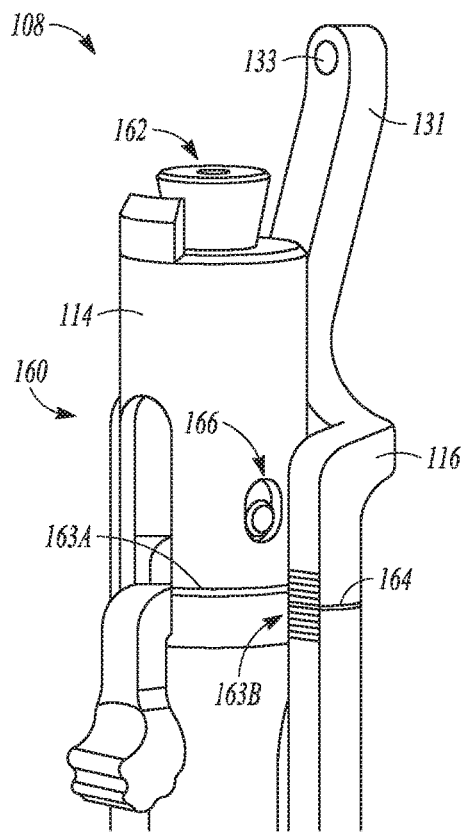
FIG. 8A is a perspective view of a tibial cut guide locking mechanism of the alignment guide according to an example of the present application.

FIG. 8A shows a proximal portion 160 of the proximal assembly 108. As shown in FIG. 8A, the first body 114 can include a coupling mechanism 162. The second body 116 can include the arm 131 extending proximally and having the through hole 133 configured to receive a fastener. As shown in the example of FIG. 8A, both the first body 114 and the second body 116 can have indicia 163A and 163B, respectively. When used together, the indicia 163A and 163B are indicative of an amount of proximal-distal travel of the first body 114 relative to the second body 116. According to one example, the indicia 163A can comprise a reference line while the indicia 163B can comprise a series of 1.0 mm separated lines and additionally a reference line 164 indicating a neutral position. As shown in FIG. 8A, the indicia 163B can indicate ±5.0 mm relative to the neutral position. The indicia 163A and 163B can be used with adjustment of the first body 114 relative to the second body 116 using the second mechanism 112 (FIGS. 7A-7D) after pinning the second body 116 to the tibia via through hole 133 as previously discussed.

The coupling mechanism 162 is configured to engage with and be actuated to couple the tibial cut guide 134 (FIGS. 4 and 9 to 10D). The coupling mechanism 162 shown in FIG. 8A includes a slot 166 and pin 168 and is further illustrated and described with reference to FIGS. 8B and 8C. The slot 166 can allows for an amount of proximal-distal travel of the pin 168 as will be discussed subsequently. Coupling mechanisms that may be constructed and/or operate in a similar manner as the coupling mechanism 162 are described in United States Patent Application Pub. 2013/0204260, U.S. patent application Ser. No. 15/184,016, and U.S. Provisional Patent Application Ser. No. 62/254,474, the entire disclosures of which are incorporated herein by reference.

Figure 8B:
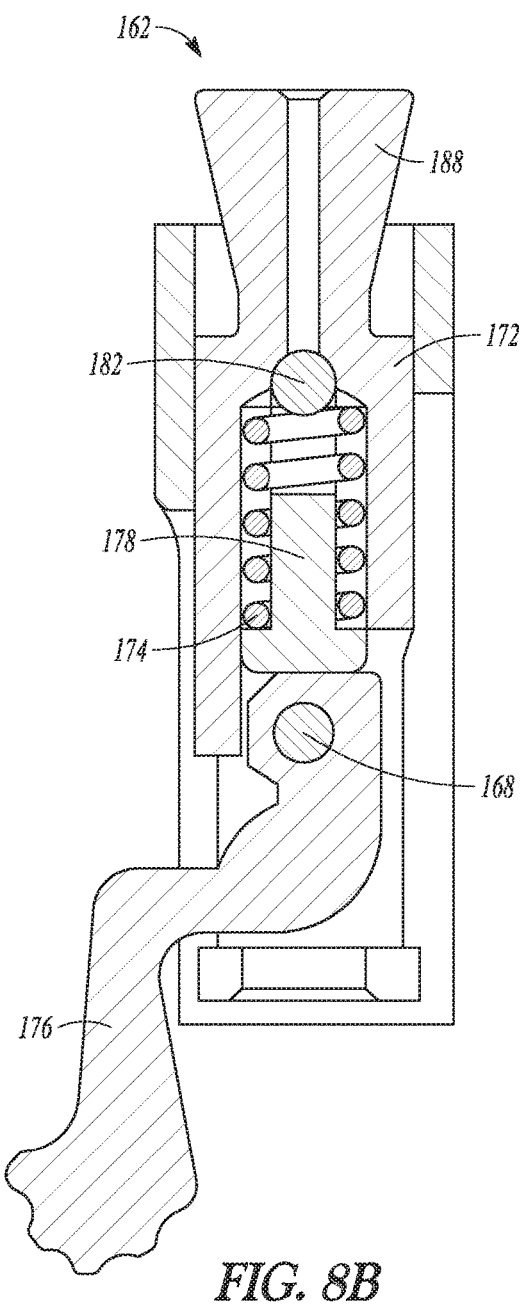
FIG. 8B is a cross-sectional view of the tibial cut guide locking mechanism of FIG. 8A according to an example of the present application.

Turning to FIG. 8B, the coupling mechanism 162 can include a housing 170, a body component 172, a spring 174, a lever 176, a member 178 and first and second pins 168, 182. The body component 172 of the coupling mechanism 162 can include first and second slots 184, 186 (only shown in FIG. 8C).

As illustrated in FIG. 8B, the housing 170 can comprise a hollow containment member having openings at both the proximal end and a distal side thereof. The body component 172 can reside therein, and can have a conic head portion 188 that extends therefrom on a proximal end. As will be discussed, the body component 172 can be moveable relative to the housing 170 in a constrained manner. The spring 174 can be positioned within the body component 172 (between the first pin 168 and an inferior surface of a head of the member 178). The member 178 can be contacted on a superior surface of the head by the surfaces of lever 176. The lever 176 can extend from the distal side opening of the housing 170 and a distal side opening of the body component 172 as shown in FIG. 8B a. The second pin 182 can be can be received in an aperture or slot of the body component 172. The first pin 168 can be received in the slot 168 of the housing 170 and can be received in the first slot 184 of the body component 172.

Figure 8C:
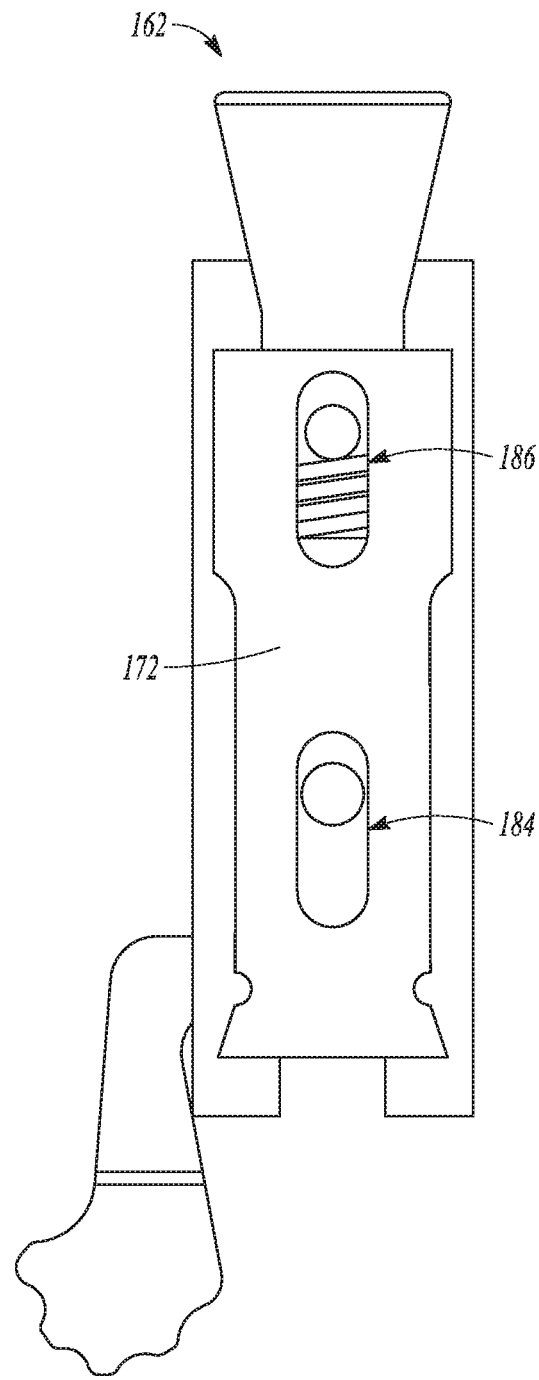
FIG. 8C is a plan view with portions of a housing of the tibial cut guide locking mechanism removed to illustrate a body component residing therein according to an example of the present application.

In operation, the lever 176 can be actuated upward (pivoting about the first pin 168) away from the position shown in FIGS. 8A to 8C to unlock the coupling mechanism 162 to facilitate removal of and/or addition of the tibial cut guide, which is mounted to a conic head portion 188. Movement of the lever 176 can allow the body component 172 to be translated upward relative to the housing 170. The spring 174 may not be constrained until the first pin 168 contacts the proximal end of the slot 166 in the housing 170. With movement of the body component 172 proximally, the conic head portion 188 has sufficient clearance relative to a proximal end portion of the housing 170 such that a mating female conic portion of the tibial cut guide can be mounted to the body component 172 and the housing 170. When the lever 176 is pivoted back to the distal position illustrated in FIGS. 8A to 8C, a conic lock between the cut guide and the conical head portion 188 is maintained by the spring 174 such that the male conic portion 188 is in fully engaged contact and is seated with the female conic portion located on the tibial cut guide. The projection 190 extending proximally from the proximal end of the housing 170 can be configured to fit in a female counterpart slot or recess in the tibial cut guide. In this manner, the body component 172 and the housing 170 can constrain the proximal-distal and rotational movement of the tibial cut guide.

Figure 9:
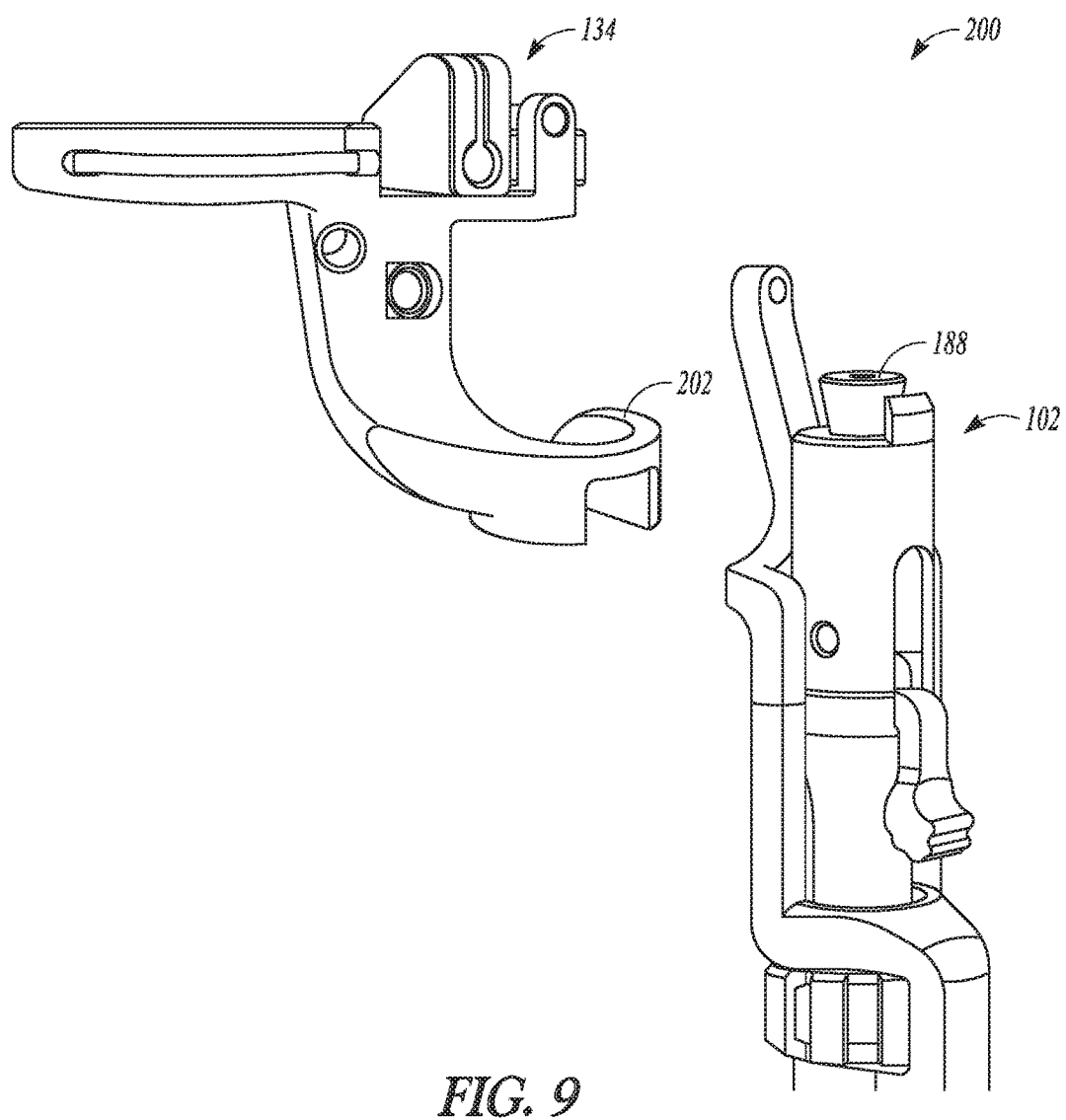
FIG. 9 shows a tibial cut guide disposed adjacent the tibial alignment guide and configured to be coupled therewith according to an example of the present application.

FIG. 9 shows a system 200 including the tibial cut guide 134 and the tibial alignment guide 102 as previously discussed. The tibial cut guide 134 can include a mount 202 configured to couple with the male conic portion 188 of the tibial cut guide 102 as previously described.

The tibial cut guide 134 is further illustrated in reference to FIGS. 10A to 10D. The tibial cut guide 134 can include a first guide portion 204 and a second guide portion 206.

The mount 202 can connect to and indeed can be formed as port of the second guide portion 206. The first guide portion 204 can be coupled to and can be adjustable relative to the second guide portion 206. The first guide portion 204 can configured to define a sagittal cut slot 208. The second guide portion is configured to define a proximal cut slot 210. The sagittal cut slot 208 and the proximal cut slot 210 are configured to limit travel and orient a sagittal resection and a proximal resection, respectively, when performed on the tibia. Such cuts can be performed using known cutting tools. According to the example of FIGS. 10A to 10D, the tibial cut guide 134 can be configured for resection of a single compartment of the tibia. More particularly, the proximal cut slot 210 can be offset from the mount 202 of the second guide portion 206 in at least one of a medial or lateral direction. The proximal cut slot 210 can be configured to define a medial-lateral cut length such that the proximal cut is to a single compartment of a knee.

Figure 10A:
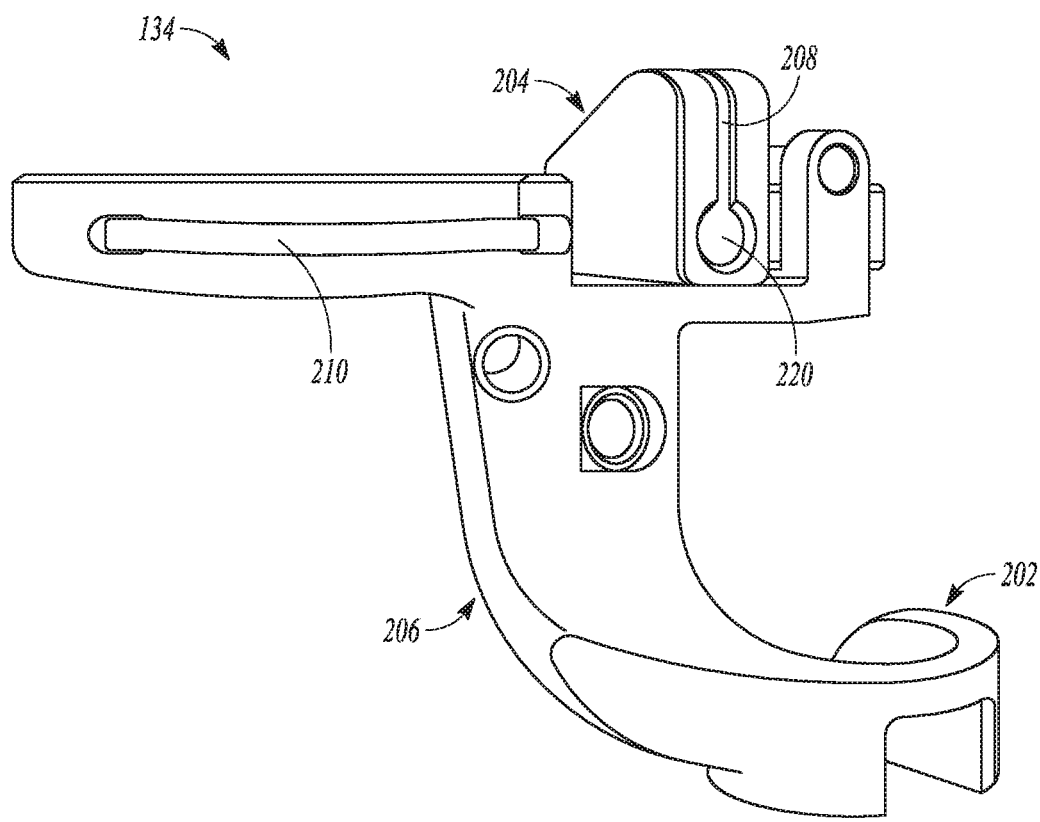
FIG. 10A-10D are views of the tibial cut guide of FIG. 9 from various perspectives according to an example of the present application.
Figure 10B:
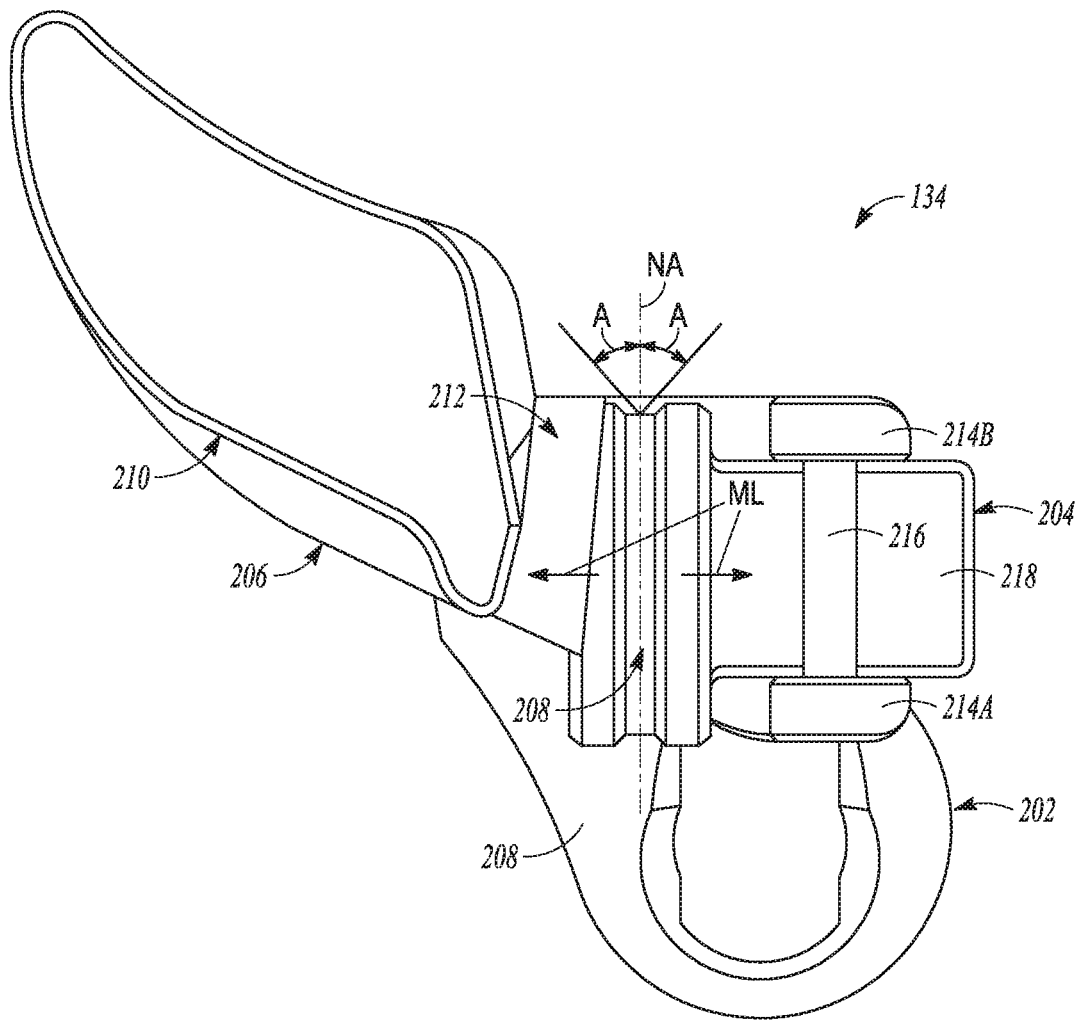

As shown by arrows in FIG. 10B, the first guide portion 204 can be configured to be adjustable both with respect to a medial-lateral position (as shown by arrow ML) and a rotational position (as shown by arrow A) relative to the second guide portion 206. Changing the rotational position of the first guide portion 204 can change the angle of the sagittal cut slot 208 from the neutral position shown in FIGS. 10B and 10C such that the sagittal cut slot 208 can be angled (i.e. canted) to extend, a medial-lateral distance, a proximal-distal distance and an anterior-posterior distance. In the neutral position, the sagittal cut slot 208 can be oriented to extend substantially only the proximal-distal distance and anterior-posterior distance. The change in angle can be of varying degree as desired. The angle of the sagittal cut slot 208 can be changed ±1°, 3°, or 5° relative to the neutral position shown in FIGS. 10B and 10C, for example. Similar, the position of the sagittal cut slot 208 can be changed medial-lateral by ±1.0, 3.0, or 5.0 mm relative to the neutral position shown in FIGS. 10B and 10C.

Figure 10C:
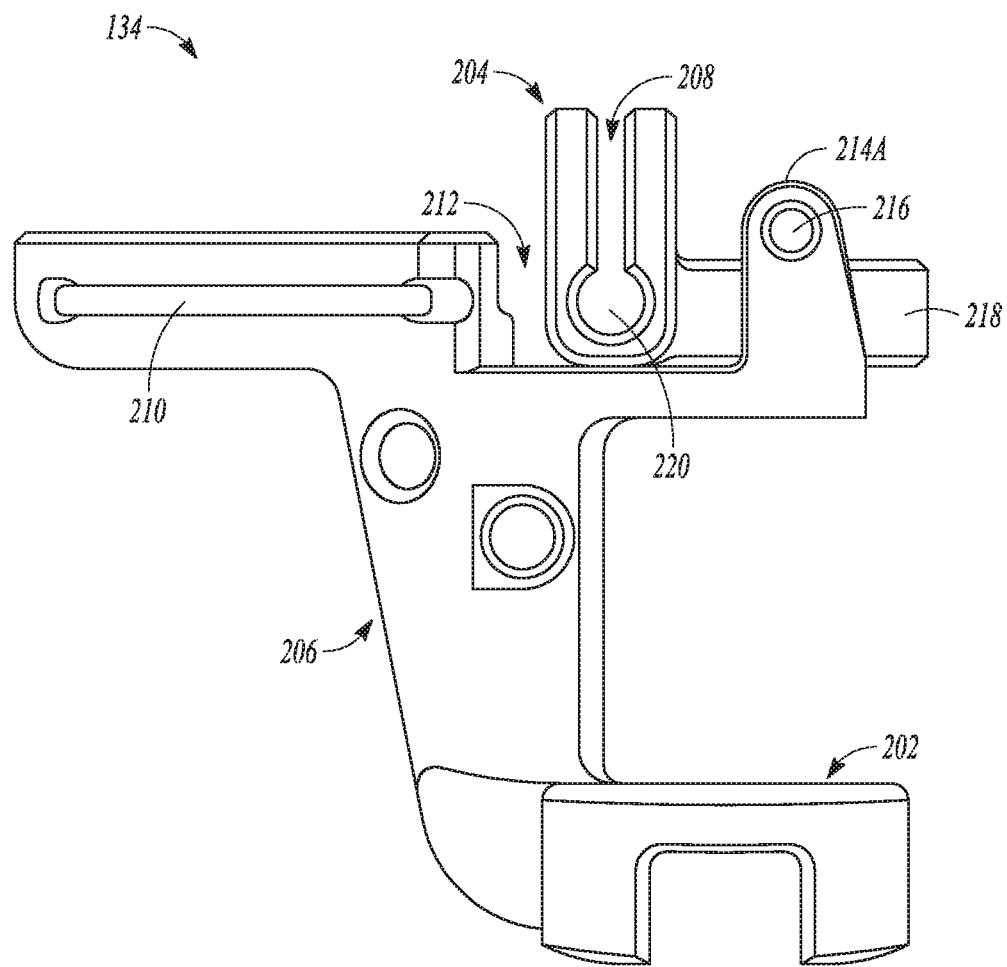
Figure 10D:
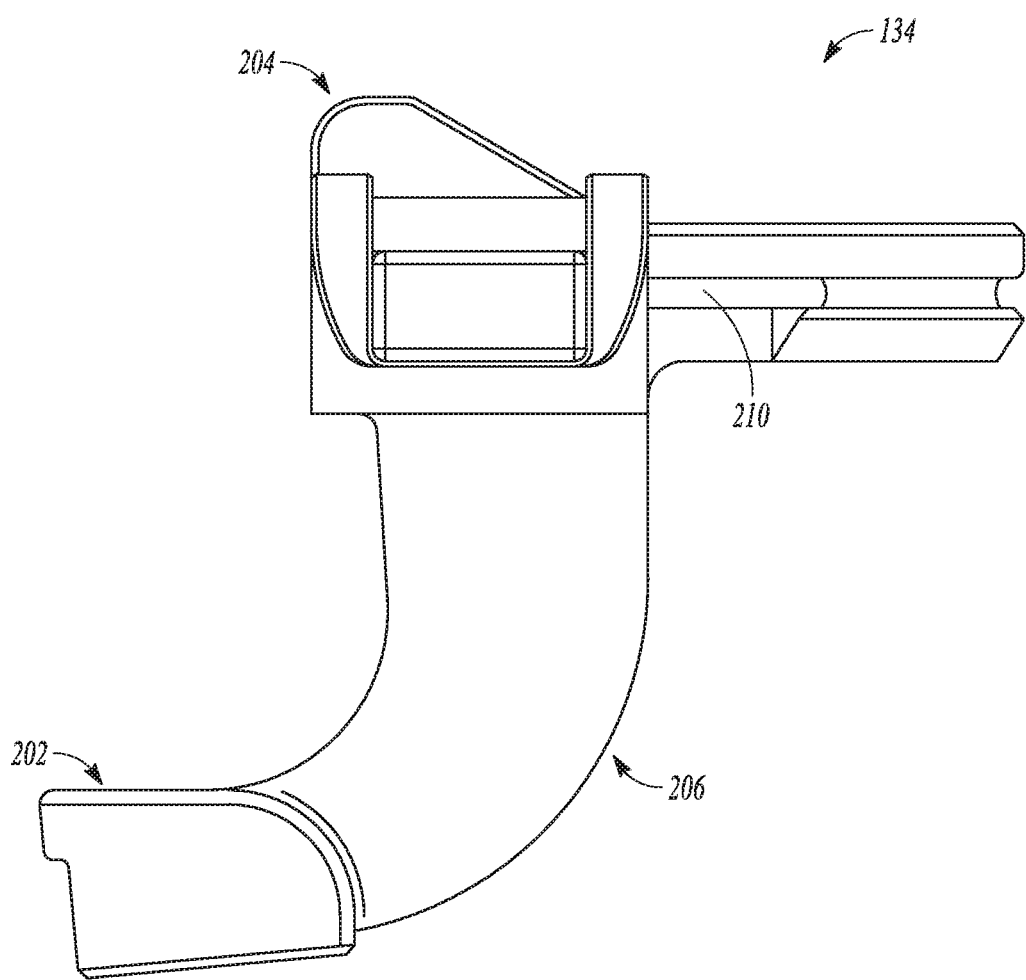

FIGS. 10B and 10C further show that the second guide portion 206 can define a recess 212 relative to the proximal cut slot 210. The recess 212 can be configured to receive the first guide portion 204 therein. The recess 212 can be open along a portion of the medial-lateral length thereof, but can be at least partially defined by along such length by anterior-posterior spaced projections 214A, 214B configured to receive a pin 216 therein. The first guide portion 204 can be configured with a leg 218 that can be configured to insert between the anterior-posterior spaced projections 214A, 214B and beneath the pin 216. The tibial cut guide 200 can be configured with some degree of freedom between the leg 218, the anterior-posterior spaced projections 214A, 214B, and the pin 216 to allow for the adjustment of the rotational position and/or the medial-lateral position of the first guide portion 204 relative to the second guide portion 206 as previously described.

As shown in FIGS. 10A and 10C, the sagittal cut slot 208 can communicate with an aperture 220. The aperture 220 can be configured to receive a fastener therein to fix the first guide portion 204 relative to the tibia and the second guide portion 206. The fastener or other feature, when received in the aperture 220, can act as a stop for a cutting tool making a sagittal resection of the tibia.

With reference to the FIGURES presented herein, a method for performing a tibial knee resection is also disclosed herein. The method can include mounting a tibial cut guide to an alignment mechanism. The tibial cut guide can be configured to facilitate both a proximal cut and a sagittal cut to a tibia. The method can adjust a proximal-distal location and varus-valgus location for a first slot that is used to define the proximal cut. A first portion of the alignment guide can be fixated to the tibia of the patient. Such step of fixation can occur after adjusting the proximal-distal location and varus-valgus location for the first slot as desired according to one example. After fixating the first portion of the alignment guide to the tibia, the method can adjust a proximal-distal height of the cut guide by extending or retracting a second portion of the alignment guide relative to the first portion of the alignment guide. Such extending and retracting can be in a generally proximal-distal direction according to one example. After adjusting the proximal-distal height of the cut guide, the method can adjust at least one of a medial-lateral location and a rotational angle of a second slot of the tibial cut guide that is used to define the sagittal cut by moving a first guide portion of the tibial cut guide relative to a second guide portion with reference to one or more anatomical landmarks of the knee. According to some examples, after adjusting the at least one of the medial-lateral location and the rotational angle of the second slot that can be used to define the sagittal cut, the method can fixate the first guide portion to the tibia prior to resecting the tibia. Resection of the tibia can be accomplished by performing both the proximal cut and the sagittal cut utilizing the tibial cut guide. The anatomical landmarks used with the method can include one or more of the intercondylar eminence of the tibia, a connection position of an ACL with the tibia, a medial third of a tubercle at insertion of a PCL, and an intercondylar geometry of a femur according to one example.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for a knee replacement surgery comprising:
a tibial cut guide having a first guide portion coupled to and adjustable relative to a second guide portion, wherein the first guide portion is configured to define a sagittal cut slot and the second guide portion is configured to define a proximal cut slot; and
an alignment guide configured for extramedullary mounting to the patient and configured to couple with the second guide portion of the tibial cut guide, the alignment guide having a first mechanism and a second mechanism of differing construction, the first mechanism and the second mechanism are both configured to be actuated to facilitate extension and retraction of the alignment guide to position the tibial cut guide in a desired proximal-distal location relative a tibia of a patient when the tibial cut guide and the alignment guide are assembled together;
wherein the alignment guide includes a proximal assembly and a distal assembly, the distal assembly includes a rod having one or more engagement features along at least a portion thereof, wherein the proximal assembly is configured to be moveable relative to the distal assembly and includes a slot configured to receive at least a part of the rod therein, wherein the proximal assembly has an arm extending proximally, the arm configured to receive a fastener therein to couple the alignment guide to the tibia of the patient, and wherein the proximal assembly has a first body and a second body, and wherein the first body is moveable relative to the second body by the second mechanism.

2. The system of claim 1, wherein the distal assembly is configured to couple with the first mechanism which comprises a button that is configured to be depressible to facilitate adjustment of the proximal assembly relative to the distal assembly, the button configured to engage the one or more engagement features of the distal assembly.

3. The system of claim 1, wherein the second mechanism comprises a thumb screw configured to threadably engage the first body and be received within a recess of the second body.

4. The system of claim 3, wherein the thumb screw is configured to retain one or more ball plunger assemblies and the second body is configured with one or more grooves that are configured to interact with the one or more ball plunger assemblies to act as indicia of a degree of movement of the second mechanism and an amount of proximal-distal travel of the first body relative to the second body.

5. The system of claim 1, wherein both the first body and the second body have indicia that when used together are indicative of an amount of proximal-distal travel of the first body relative to the second body.

6. The system of claim 1, wherein the first guide portion of the tibial cut guide is configured to be adjustable both with respect to a medial-lateral position and a rotational position relative to the second guide portion.

7. The system of claim 1, wherein the second guide portion defines a recess relative to the proximal cut slot, the recess is configured to receive the first guide portion therein, wherein the recess is at least partially defined by anterior-posterior spaced projections configured to receive a pin therein, and wherein a leg of the first guide portion is configured to insert between the anterior-posterior spaced projections and beneath the pin.

8. The system of claim 1, wherein the sagittal cut slot communicates with an aperture, and wherein the aperture is configured to receive a fastener therein to fix the first guide portion relative to the tibia and the second guide portion.

9. The system of claim 1, wherein the proximal cut slot is offset from a mount of the second guide portion in at least one of a medial or lateral direction and the proximal cut slot isconfigured to define a medial-lateral cut length such that the proximal cut is to a single compartment of a knee.

10. An apparatus for guiding a tibial bone cut during knee replacement surgery, the apparatus comprising:
a mount configured to couple with an alignment guide;
a proximal guide portion connected to the mount and configured to define a proximal cut slot, wherein the proximal cut slot is offset from the mount in at least one of a medial or lateral direction and the proximal cut slot is configured to define a medial- lateral cut length such that the proximal cut is to a single compartment of a knee; and
a sagittal guide portion coupled to and adjustable relative to the proximal guide portion, wherein the sagittal guide portion is configured to define a sagittal cut slot;
wherein the proximal guide portion defines a recess relative to the proximal cut slot, the recess is configured to receive the sagittal guide portion therein, wherein the recess is at least partially defined by anterior-posterior spaced projections configured to receive a pin therein, and wherein a leg of the sagittal guide portion is configured to insert between the anterior-posterior spaced projections and beneath the pin.

11. The apparatus of claim 10, wherein the sagittal guide portion is configured to be adjustable both with respect to a medial-lateral position and a rotational position relative to the proximal guide portion.

12. The apparatus of claim 10, wherein the sagittal cut slot communicates with an aperture, and wherein the aperture is configured to receive a fastener therein to fix the first guide portion relative to the tibia.

13. An alignment guide configured for extramedullary mounting to a patient for a knee replacement surgery, the alignment guide comprising:
a first portion having a rod with one or more engagement features along at least a portion thereof;
a second portion moveable relative to the first portion and having a slot configured to receive at least a part of the rod therein, the second portion configured to receive at least a part of a first mechanism and a second mechanism, the first mechanism configured to be actuated facilitate proximal-distal adjustment of the second portion relative to the first portion; and a third portion at least partially received by the second portion and moveable relative thereto, the third portion configured to couple with a tibial cut guide, wherein the second mechanism is configured to be actuated to facilitate proximal-distal adjustment of the third portion relative to the second portion;

wherein the second mechanism comprises a thumb screw configured to threadably engage the third portion and be received within a recess of the second portion; and wherein the thumb screw is configured to retain one or more ball plunger assemblies and the second portion is configured with one or more grooves that interact with the one or more ball plunger assemblies to act as indicia of a degree of movement of the second mechanism and an amount of proximal-distal travel of the third portion relative to the second portion.

14. The guide of claim 13, wherein the first adjustment member and the second mechanism have a differing construction but are both configured to allow the alignment guide to be extended and retracted to position the tibial cut guide in a desired proximal-distal location relative a tibia of a patient.

15. The guide of claim 13, wherein the second portion has an arm configured to receive a fastener therein to couple the alignment guide to the tibia of the patient.

16. The system of claim 13, wherein both the third portion and the second portion have indicia that when used together are indicative of an amount of proximal-distal travel of the third portion relative to the second portion.

17. A method of performing a tibial knee resection comprising:

mounting a tibial cut guide to an alignment mechanism, the tibial cut guide configured to facilitate both a proximal cut and a sagittal cut to a tibia;

adjusting a proximal-distal location and varus-valgus location for a first slot that is used to define the proximal cut;

fixating a first portion the alignment guide to the tibia of the patient;

after fixating the first portion of the alignment guide to the tibia, adjusting a proximal-distal height of the cut guide by extending or retracting a second portion of the alignment guide relative to the first portion of the alignment guide;

after adjusting the proximal-distal height of the cut guide, adjusting at least one of a medial-lateral location and a rotational angle of a second slot that is used to define the sagittal cut by moving a first guide portion of the tibial cut guide relative to a second guide portion with reference to one or more anatomical landmarks of the knee; and resecting the tibia by performing both the proximal cut and the sagittal cut utilizing the tibial cut guide.

18. The method of claim 17, further comprising fixating the first guide portion to the tibia prior to resecting the tibia.

19. The method of claim 17, wherein the anatomical landmarks include one or more of the intercondylar eminence of the tibia, a connection position of an ACL with the tibia, a medial third of a tubercle at insertion of a PCL, and an intercondylar geometry of a femur.

* * * * *